United States Patent [19]

Hellring et al.

[11] Patent Number: 5,583,276
[45] Date of Patent: Dec. 10, 1996

[54] PROCESS FOR PRODUCING LOW AROMATIC DIESEL FUEL WITH HIGH CETANE INDEX

[75] Inventors: Stuart D. Hellring, Yardley; Charles T. Kresge, West Chester, both of Pa.; David O. Marler, Deptford, N.J.; Ernest W. Valyocsik, Yardley, Pa.

[73] Assignee: Mobil Oil Corporation, Fairfax, Va.

[21] Appl. No.: 442,549

[22] Filed: May 16, 1995

Related U.S. Application Data

[63] Continuation-in-part of Ser. No. 205,437, Mar. 4, 1994, Pat. No. 5,437,855, which is a continuation-in-part of Ser. No. 137,705, Oct. 18, 1993, abandoned.

[51] Int. Cl.$^6$ .................................................. C07C 2/58
[52] U.S. Cl. ........................................ 585/722; 585/709
[58] Field of Search ................................. 585/722, 709

[56] References Cited

U.S. PATENT DOCUMENTS

| | | | |
|---|---|---|---|
| Re. 28,398 | 4/1975 | Chen et al. | 208/111 |
| 3,668,113 | 6/1972 | Burbidge et al. | 208/97 |
| 3,755,138 | 8/1973 | Chen et al. | 208/33 |
| 3,917,564 | 11/1975 | Meyers | 208/131 |
| 3,956,102 | 5/1976 | Chen et al. | 208/93 |
| 3,960,978 | 6/1976 | Givens et al. | 260/683.15 R |
| 4,021,502 | 5/1977 | Plank et al. | 260/683.15 R |
| 4,100,056 | 7/1978 | Reynolds | 208/57 |
| 4,100,218 | 7/1978 | Chen et al. | 260/673 |
| 4,150,062 | 4/1979 | Garwood et al. | 260/673 |
| 4,211,640 | 7/1980 | Garwood et al. | 208/255 |
| 4,227,992 | 10/1980 | Garwood et al. | 208/46 |
| 4,400,265 | 8/1983 | Shen | 208/97 |
| 4,422,185 | 12/1983 | Cook | 2/8 |
| 4,456,781 | 6/1984 | Marsh et al. | 585/533 |
| 4,483,760 | 11/1984 | Tabak et al. | 208/60 |
| 4,874,505 | 10/1989 | Bartilucci et al. | 208/131 |
| 4,922,048 | 5/1990 | Harandi | 585/310 |
| 4,922,051 | 5/1990 | Nemet-Mavrodin et al. | 585/418 |
| 5,227,552 | 7/1993 | Chang et al. | 585/257 |
| 5,258,569 | 11/1993 | Chu et al. | 585/722 |
| 5,365,000 | 11/1994 | Kresge et al. | 585/722 |
| 5,437,855 | 8/1995 | Valyocsik | 423/718 |
| 5,461,182 | 10/1995 | Hellring et al. | 585/722 |

FOREIGN PATENT DOCUMENTS

WO94/03415  2/1994  WIPO .................................. 585/722

OTHER PUBLICATIONS

Albright, L. F. et al., "Alkylation of Isobutane with C$_4$ Olefins," 27 *Ind. Eng. Chem. Res.*, 381–386, 1988.
*The Handbook of Petroleum Refining Processes*, 23–28 R. A. Meyers, ed., 1986.
*Hydrocarbon Processing*, vol. 61, No. 5, May 1982 pp. 110–112.
*Hydrocarbon Processing*, vol. 60, No. 9, Sep. 1981, pp. 134–138.
*The Oil and Gas Journal*, Jan. 6, 1975 pp. 69–73.

*Primary Examiner*—Asok Pal
*Attorney, Agent, or Firm*—Malcolm D. Keen; Lori F. Cuomo

[57] ABSTRACT

A process for converting at least one olefin and at least one isoparaffin to a diesel fuel blending component comprising the steps of contacting the olefin and the isoparaffin with a catalyst comprising MCM-58 to provide a diesel fuel. Process conditions can be varied to favor the formation of gasoline, distillate, lube range products or mixtures thereof.

16 Claims, No Drawings

5,583,276

PROCESS FOR PRODUCING LOW AROMATIC DIESEL FUEL WITH HIGH CETANE INDEX

CROSS REFERENCE TO RELATED APPLICATIONS

This application is a continuation in part of U.S. application Ser. No. 08/205,437, filed Mar. 4, 1994, now U.S. Pat. No. 5,437,855, entirely incorporated herein by reference, which is a continuation in part of U.S. application Ser. No. 08/137,705, filed Oct. 18, 1993, now abandoned entirely incorporated herein by reference.

FIELD OF THE INVENTION

The present invention relates to a process for producing low aromatic diesel fuel with a high cetane index. Particularly, the invention relates to a process for selectively upgrading lower boiling range feedstocks into higher boiling range fuels having a desired composition.

BACKGROUND OF THE INVENTION

Recent regulatory developments have led refiners to seek methods for reformulating motor fuels, including gasoline and diesel fuel, to meet increasingly stringent air quality requirements. These techniques include reducing the olefin and aromatic content of the motor fuels while maintaining the desired operational characteristics as predicted by the octane or cetane rating of the fuel.

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate.

Industrial alkylation processes have historically used large volumes of liquid Bronsted acid catalysts such as hydrofluoric or sulfuric acid under relatively low temperature conditions. Acid strength is preferably maintained at 88 to 94 weight percent by the continuous addition of fresh acid and the continuous withdrawal of spent acid. Liquid acid catalyzed isoparaffin:olefin alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

The typical petroleum refinery generates numerous olefinic streams, which, upon hydrogenation and optional fractionation, would be useful gasoline blending components. Examples of such streams include the olefinic gasoline and naphtha by-products of catalytic hydrodewaxing processes such as the MLDW (Mobil Lubricant Dewaxing) and MDDW (Mobil Distillate Dewaxing). Additional examples include olefinic gasoline cuts from delayed coking units (thermally cracked gasoline), as well as from catalytic cracking process units such as a Fluidized Catalytic Cracking (FCC) process. Lighter olefins may be easily dimerized or oligomerized to provide suitable feedstocks, for example in a process such as MOGD/MOGDL (Mobil Olefins to Gasoline and Distillate/Mobil Olefins to Gasoline, Distillate and Lube Stock), or MOCI (Mobil Olefins to Chemical Intermediates). Examples of processes which product olefinic stocks include the processes taught in U.S. Pat. Nos. 4,922,048 to Harandi and 4,922,051 to Nemet-Mavrodin et al. Additional examples of light olefin dimerization/oligomerization processes include Dimersol (light olefin dimerization), Isopol (selective isobutene isomerization) and Selectopol (selective butadiene polymerization). See *Hydrocarbon Processing*, Vol. 61, No. 5, May 1982, pp. 110–112, and *Hydrocarbon Processing*, Vol. 60, No. 9, Sep. 1981, pp. 134–138.

Recent regulatory changes have created an incentive for refiners to reduce the olefins and aromatics content of motor fuels. The final version of the complex model issued by the United States Environmental Protection Agency (US EPA) to predict the consequence of various fuel components on combustion emissions creates a significant penalty for high RVP components in gasoline. At the same time, both the US EPA and state regulatory boards such as the California Air Resources Board (CARB) have instituted regulations on diesel fuel which set an upper limit on aromatics and sulfur contents, and a lower limit for cetane index. In general, sulfur must remain below 500 ppm. U.S. EPA requires either less than 35 wt % aromatics or a minimum of 40 cetane index. CARB limits aromatics to 10 wt % unless a waiver fuel is approved. Both regulatory agencies require a maximum $T_{90}$ of 640° F. By alkylating light olefins, such as $C_3$–$C_5$ olefins, with light isoparaffins, such as isobutane and isopentane, high RVP gasoline components are converted into diesel range fuel which meets most of the regulatory restrictions.

SUMMARY OF THE INVENTION

A mixed stream of isoparaffin, such as isobutane or isopentane, and olefins, such as propylene, butenes, pentenes, or hexenes, are passed over a zeolite catalyst comprising MCM-58 in a fixed-bed under pressure at sufficiently high temperature to produce diesel range fuel. Process conditions can be varied to favor the formation of either gasoline, distillate, lube range products or mixtures thereof.

The feed olefins can come from among many sources including FCC olefins, MTBE raffinate, TAME raffinate, etc. A detailed description of possible olefins sources is outlined in U.S. Pat. No. 5,227,552, to Chang, Hellring and Striebel, which is incorporated by reference as if set forth at length herein. The isoparaffin can come from FCC, hydrocracking, etc. process or by isolation of field production off-gases. Generally, $C_4$–$C_8$ isoparaffins and preferably $C_4$–$C_5$ isoparaffins are used in the present invention.

DETAILED DESCRIPTION

Olefinic feedstocks suitable for use in the present invention include numerous olefinic streams produced by petroleum refining operations, for example, a cracked olefinic stream such as an olefinic gasoline boiling range fraction from a delayed coker process unit. The olefinic feedstocks generally comprises $C_2$–$C_{10}$ olefins and preferably $C_3$–$C_8$ olefins. Delayed coking processes are taught in U.S. Pat. No. 3,917,564 to Meyers and U.S. Pat. No. 4,874,505 to Bartilucci et al., both of which patents are incorporated herein by reference.

Suitable olefinic feedstocks are also produced as byproducts in catalytic dewaxing processes, as described in U.S. Pat. No. 4,922,048, which patent is incorporated herein by reference.

Catalytic dewaxing of hydrocarbon oils to reduce the temperature at which precipitation of waxy hydrocarbons occurs is a known process and is described, for example, in the Oil and Gas Journal, Jan. 6, 1975, pages 69–73. A number of patents have also described catalytic dewaxing processes. For example, U.S. Pat. RE. No. 28,398 describes a process for catalytic dewaxing with a catalyst comprising a medium-pore zeolite and a hydrogenation/dehydrogenation component. U.S. Pat. No. 3,956,102 describes a process for hydrodewaxing a gas oil with a medium-pore zeolite catalyst. U.S. Pat. No. 4,100,056 describes a Mordenite catalyst containing a Group VI or a Group VIII metal which may be used to dewax a distillate derived from a waxy crude. U.S. Pat. No. 3,755,138 describes a process for mild solvent dewaxing to remove high quality wax from a lube stock, which is then catalytically dewaxed to specification pour point. Such developments in catalytic dewaxing have led to the MLDW (Mobil Lube Dewaxing) and MDDW (Mobil Distillate Dewaxing) process.

Catalytic dewaxing processes may be followed by other processing steps such as hydrodesulfurization and denitrogenation in order to improve the qualities of the product. For example, U.S. Pat. No. 3,668,113 describes a catalytic dewaxing process employing a Mordenite dewaxing catalyst which is followed by a catalytic hydrodesulfurization step over an alumina-based catalyst. U.S. Pat. No. 4,400,265 describes a catalytic dewaxing/hydrodewaxing process using a zeolite catalyst having the structure of ZSM-5 wherein gas oil is catalytically dewaxed followed by hydrodesulfurization in a cascade system. The foregoing dewaxing processes exemplify low-severity medium-pore catalyzed dewaxing processes which produce a low octane naphtha by-product. Another example of a low severity medium-pore catalyzed conversion reaction is olefin oligomerization.

Recent developments in zeolite catalysts and hydrocarbon conversion methods and apparatuses have created interest in utilizing olefinic feedstocks for producing heavier hydrocarbons, such as $C_5+$ gasoline, distillate or lubes. These developments form the basis of the Mobil olefins to gasoline/distillate (MOGD) method and apparatus, and the Mobil olefins to gasoline/distillate/lubes (MOGDL) method and apparatus.

In MOGD and MOGDL, olefins are catalytically converted to heavier hydrocarbons by catalytic oligomerization using an acid crystalline zeolite, such as a zeolite catalyst having the structure of ZSM-5. Process conditions can be varied to favor the formation of either gasoline, distillate or lube range products. U.S. Pat. Nos. 3,960,978 and 4,021,502 to Plank et al. disclose the conversion of $C_2$–$C_5$ olefins alone or in combination with paraffinic components, into higher hydrocarbons over a crystalline zeolite catalyst. U.S. Pat. Nos. 4,150,062; 4,211,640 and 4,227,992 to Garwood et al. have contributed improved processing techniques to the MOGD system. U.S. Pat. No. 4,456,781 to Marsh et al. has also disclosed improved processing techniques for the MOGD system.

U.S. Pat. Nos. 4,422,185 and 4,483,760 to Tabak disclose two-stage catalytic processes for upgrading hydrocarbon feedstocks, the texts of which are incorporated by reference as if set forth at length herein.

The '185 patent to Tabak teaches a process for converting an olefinic feedstock containing ethene and heavier alkenes to a product rich in distillate and olefinic gasoline. Effluent from a first stage distillate mode reactor is flashed to separate an ethylene-rich product stream which is then charged to a second stage gasoline mode reactor. A disadvantage of the process taught by '185 is that the highly olefinic gasoline product stream is of a relatively low octane and reduces the gasoline pool octane.

The '760 patent to Tabak teaches a process for catalytically dewaxing a middle distillate separating an olefinic by-product from the dewaxed distillate product stream, and upgrading a gasoline fraction at temperatures above 900° F. In addition, the second catalytic reactor is operated to convert at least 10 wt. % of the olefinic by-product fraction to fuel oil (material boiling above 380° F.).

Olefinic feedstocks may be obtained from various sources, including from fossil fuel processing streams such as gas separation units, from the cracking of $C_2$-hydrocarbons, such as LPG (liquified petroleum gas) from coal by-products, from various synthetic fuel processing streams, and as by-products from fluid catalytic cracking (FCC) and thermal catalytic cracking (TCC) process units. U.S. Pat. No. 4,100,218 to Chen et al. teaches thermal cracking of ethane to ethylene, with subsequent conversion of ethylene to LPG and gasoline over a zeolite catalyst having the structure of ZSM-5.

Distillate products produced over a broad range of conversion conditions useful in the present process have a cetane index of at least about 35 and preferably have at least about a 45 cetane index.

Conversion is inversely proportional with $WHSV_{olefin\ on\ zeolite}$ for a given temperature. Between 0.1 and 1.0 WHSV, reactor temperature must be above about 350° F. in order to achieve $C_5$-olefin conversions above 90%. If temperature is restricted to 375° F. to limit aromatics to 10 wt %, $WHSV_{olefin\ on\ zeolite}$ must be held below about 0.3 to maintain 90% or greater pentenes conversion.

The term "yield" as used herein is defined as the weight of product per weight of converted olefin. Total product yields above unity indicate that isoparaffin has been incorporated into the products. Maximum gasoline yield in isobutane/butene alkylation results from combination of one mole of each reactant to provide a yield slightly above 2.0. Ideally, a diesel range fuel is produced by reacting more than one mole of olefin per isoparaffin. For instance, a mole of isobutane must combine with two or three moles of butene to reach sufficient molecular weight to enter the boiling range of diesel fuel. Likewise, a mole of isopentane would require two moles of pentene to reach diesel range and would give a yield of about 1.5. Therefore, diesel production in the present invention uses a lower isoparaffin/olefin molar ratio than typically is used for producing gasoline from a similar reactor feed stream.

Process Conditions

|  | Broad Range | Preferred Range |
| --- | --- | --- |
| Temperature | 100–500° F. | 200–400° F. |
| Pressure | 0–1500 psig | 50–1000 psig |
| Olefin WHSV (Zeolite Basis) | 0.01–10 | 0.1–5.0 |
| Isoparaffin:Olefin Molar Ratio in Feedstock | 0.1–100 | 0.25–50 |

The product slates can be adjusted by varying the operating conditions. In general higher cetane index of the diesel range product is favored by higher olefin WHSV and lower temperatures in the above ranges. Gasoline yields are maximized at higher temperatures and higher isoparaffin:olefin molar ratios in the above ranges. Distillate production is favored by higher isoparaffin:olefin molar ratios and lower temperatures in the above ranges.

The reaction temperature can be limited to obtain a range of aromatics content in the diesel fuel product. In cases where isopentane is reacted with pentenes, lower temperatures in the above ranges result in low wt. % aromatics in the gasoline and distillate product. To produce a diesel range blending stock containing less than about 10 wt % aromatics, the reactor temperature is preferably kept below about 375° F. To meet the 35 wt % aromatics limit set by the US EPA, reactor temperature is preferably controlled below about 440° F.

In cases where an increased amount of the distillate fraction is desired the product boiling at a cut point up to about 450° F. may be recycled to the contacting step. The product boiling at a cut point up to about 390° F. may also be recycled to the contacting step.

Optionally, the product of the present invention can be further hydrotreated by conventional methods to reduce product olefins by saturation.

The MCM-58 material for use herein has a composition involving the molar relationship:

$$X_2O_3:(n)YO_2,$$

wherein X is a trivalent element, such as aluminum, boron, iron, indium, and/or gallium, preferably aluminum; Y is a tetravalent element such as silicon, tin, and/or germanium, preferably silicon; and n is from greater than about 10 to about 1000, usually from greater than about 10 to about 400, more usually from about 20 to about 200. In the as-synthesized form, the material has a formula, on an anhydrous basis and in terms of moles of oxides per n moles of $YO_2$, as follows:

$$(0.1–2)M_2O:(0.2–2)R:X_2O_3:nYO_2$$

wherein M is an alkali or alkaline earth metal, and R is an organic moiety. The M and R components are associated with the material as a result of their presence during crystallization, and are easily removed by post-crystallization methods hereinafter more particularly described.

The MCM-58 for use in the invention is thermally stable and in the calcined form exhibits significant hydrocarbon sorption capacity. To the extent desired, the original sodium and/or potassium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In the as-synthesized form, the crystalline MCM-58 material for use in the invention appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table I below:

TABLE I

| Interplanar d-Spacing (A) | Relative Intensity, I/Io × 100 |
|---|---|
| 10.89 ± 0.30 | s–vs |
| 9.19 ± 0.30 | vw |
| 6.55 ± 0.29 | vw–w |
| 5.86 ± 0.28 | vw–w |
| 5.57 ± 0.27 | vw–w |
| 5.43 ± 0.26 | vw–w |
| 4.68 ± 0.25 | vw–m |
| 4.36 ± 0.25 | w–vs |
| 4.17 ± 0.23 | vw–m |
| 4.12 ± 0.23 | vw–s |
| 3.78 ± 0.20 | wv–s |
| 3.61 ± 0.15 | vw–w |
| 3.54 ± 0.15 | vw |
| 3.44 ± 0.15 | vw–m |
| 3.37 ± 0.15 | vw–m |
| 3.06 ± 0.15 | vw–w |
| 2.84 ± 0.15 | vw |
| 2.72 ± 0.13 | vw |
| 2.66 ± 0.12 | vw |
| 2.46 ± 0.12 | vw |
| 2.17 ± 0.10 | vw |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (80–100), s=strong (60–80), m=medium (40–60), w=weak (20–40), and vw=very weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history.

MCM-58 can be prepared from a reaction mixture containing sources of alkali or alkaline earth metal (M), e.g., sodium and/or potassium, cation, an oxide of trivalent element X, e.g., aluminum and/or boron, an oxide of tetravalent element Y, e.g., silicon, directing agent (R), and water, said reaction mixture having a composition, in terms of mole ratios of oxides, within the following ranges:

| Reactants | Useful | Preferred |
|---|---|---|
| $YO_2/X_2O_3$ | 15 to 1000 | 25 to 500 |
| $H_2O/YO_2$ | 5 to 200 | 20 to 100 |
| $OH^-/YO_2$ | 0 to 3 | 0.10 to 0.50 |
| $M/YO_2$ | 0 to 3 | 0.10 to 2 |
| $R/YO_2$ | 0.02 to 1.0 | 0.10 to 0.50 |

In this synthesis method, the preferred source of $YO_2$ comprises predominately solid $YO_2$, for example at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated SiO₂ containing about 87 wt. % silica, about 6 wt. % free H₂O and about 4.5 wt. % bound H₂O of hydration and having a particle size of about 0.02 micron) is preferred for MCM-58 formation from the above mixture. Preferably, therefore, the $YO_2$, e.g., silica, source contains at least about 30 wt. % solid $YO_2$, e.g., silica, and more preferably at least about 40 wt. % solid $YO_2$, e.g., silica.

The organic directing agent R for use herein above is either the cation benzylquinuclidinium, having a formula $C_{14}H_{20}N^+$ or the cation benzyltropanium, having a formula $C_{15}H_{22}N^+$, and may be represented as follows:

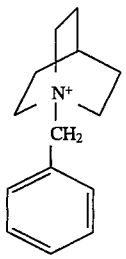

or

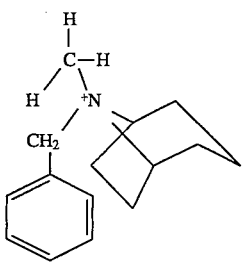

The sources of these organic cations may be, for example, the halide, e.g., chloride or bromide, or hydroxide salt. The source of organic directing agents used in the following examples was synthesized as follows:

(1) Benzylquinuclidinium halide, i.e., bromide, was synthesized by reacting benzylbromide and quinuclidine in absolute ethanol solvent in a flask equipped with a reflux condenser, a thermometer and a stirrer. The flask was charged with 60.0 grams of benzylbromide with 200 ml of absolute ethanol. Then 33.4 grams of quinuclidine dissolved in 300 ml of absolute ethanol was transferred to the flask. Heating and stirring of the flask reaction mixture commenced immediately.

The reaction mixture was refluxed (~70° C.) overnight with stirring before quenching the reaction vessel in a dry ice-acetone bath to −40° C. The cold crystalline product was separated from the solvent, filtered, and washed with anhydrous diethylether on a Büchner funnel. The crystals were dried in an air stream, then chemically analyzed. The benzylquinuclidium bromide product of this example was found to be composed of 56.13 wt. % C, 7.46 wt. % H, 4.66 wt. % N and 28.13 wt. % Br;

(2) Benzyltropanium halide, i.e., bromide, was synthesized by reacting benzylbromide and tropane in absolute ethanol solvent in a flask equipped with a reflux condenser, a thermometer and a stirrer. The flask was charged with 60.0 grams of benzylbromide with 300 ml of absolute ethanol. Then 37.6 grams of tropane dissolved in 300 ml of absolute ethanol was transferred to the flask. Heating and stirring of the flask reaction mixture commenced immediately.

The reaction mixture was refluxed (~70° C.) overnight with stirring before quenching the reaction vessel in a dry ice-acetone bath to −40° C. The cold crystalline product was separated from the solvent, filtered, and washed with anhydrous diethylether on a Büchner funnel. The benzyltropanium bromide product crystals were then dried in an air stream.

Crystallization of the MCM-58 can be carried out at either static or stirred conditions in a suitable reactor vessel, such as for example, polypropylene jars or teflon lined or stainless steel autoclaves. The total useful range of temperatures for crystallization is from about 80° C. to about 250° C. for a time sufficient for crystallization to occur at the temperature used, e.g., from about 12 hours to about 100 days. Thereafter, the crystals are separated from the liquid and recovered.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

Synthesis of MCM-58 crystals may be facilitated by the presence of at least 0.01 percent, preferably 0.10 percent and still more preferably 1 percent, seed crystals (based on total weight) of crystalline product.

The MCM-58 crystals can be shaped into a wide variety of particle sizes for use herein. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

When Alpha Value is examined, it is noted that the Alpha Value is an approximate indication of the acid catalytic activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec⁻¹). The Alpha Test is described in U.S. Pat. No. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395.

Prior to its use as catalyst in the present process, the crystalline material should be subjected to thermal treatment to remove part or all of any organic constituent present therein. This thermal treatment is generally performed by heating at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

The catalyst for use herein can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying, or partially dried and then extruded.

It may be desired to incorporate the crystalline material with another material which is resistant to the temperatures and other conditions employed in the condensation process of this invention. Such materials include active and inactive materials and synthetic or naturally occurring zeolites as well as inorganic materials such as clay, silica, and/or metal oxides such as alumina, magnesia, zirconia, thoria, beryllia, and/or titania. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that the products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with zeolite crystals include the montmorillonite and kaolin families which include the subbentonites and the kaolins commonly known as Dixie, McNamee, Georgia, and Florida clays, or others in which the main mineral constituent is halloysite, kaolinite, dickite, nacrite, or anauxite. Such clays can be used in the raw state as originally mined or initially subjected to calcination, acid treatment, or chemical modification. Binders useful for compositing with the zeolite also include inorganic oxides, notably alumina.

In addition to the foregoing materials, the crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia. It may also be advantageous to provide at least a part of the foregoing matrix materials in colloidal form to facilitate extrusion of the bound catalyst components.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The following examples illustrate the process of the present invention.

EXAMPLES

Example 1

The catalyst used in this example was an extrudate of the proton-form of MCM-58 (65%) in an alumina binder (35%). The catalyst (15.65 g) was loaded into a stainless steel tubular reactor and bracketed by vycor chips which served as heat exchangers. After placing the reactor in a tube furnace, the catalyst was dried by heating for at least two hours to at least 300° F. in a stream of flowing nitrogen. The reactor temperature was adjusted to 297° F. at 600 psig, and filled with isopentane. A pre-mixed isopentane/pentene-1 feed stream (molar ratio=9.7) then was introduced at a flow rate of 0.1 gm pentenes/gm MCM-58/hr. After passing pre-mixed feed through the reactor zone for 22.5 hrs, product was collected over the following 28 hrs. Product distributions were calculated from gc analyses of the gaseous and liquid products, and an additional simulated distillation ASTM 2887 of the liquid products. The total reactor effluent weight was 307.2 g (99.6% mass balance) and showed the following distribution:

| Component | weight % |
|---|---|
| $C_3$-minus | 0.01 |
| Isobutane | 0.11 |
| n-Butane | 0.02 |
| Isopentane | 89.66 |
| n-Pentane | 0.44 |
| Cyclopentane | 0.07 |
| $C_6$-paraffin | 0.20 |
| Methylcyclopentane | 0.01 |
| $C_4$-olefin | 0.02 |
| Butadiene | 0.00 |
| $C_5$-olefin | 3.31 |
| Cyclopentene | 0.00 |
| $C_6$-olefin | 0.56 |
| Methylcyclopentane and Benzene | 0.00 |
| $C_7$-plus | 5.59 |
| Total | 100.00 |

Conversion of total pentenes was 55.7%. Calculated yields of isobutane and $C_6$-plus components per pentenes converted (wt/wt) were:

| Fraction | Yield |
|---|---|
| $iC_4$ | 0.13 |
| $C_6$-300° F. | 0.17 |
| 300–400° F. | 0.44 |
| 400–650° F. | 0.42 |
| above 650° F. | 0.03 |
| Total | 1.19 |

About 25 g of squalane was added to a portion of the liquid product (39 g) to serve as a high boiling "chaser" during fractional microdistillation. After distilling the sample to a 300° F. endpoint at ambient atmospheric pressure, the residua were fractionated under vacuum (about 55 torr) to obtain a cut (12.3 g) with the intended kerojet boiling range from 300° F. to 400° F. The actual boiling range for this cut was estimated by simulated distillation analysis ASTM 2887. The boiling range and product properties for this sample were:

| Intended cut 300–400° F. Boiling Range (°F.) | |
|---|---|
| IBP | 202 |
| T10 | 299 |
| T50 | 328 |
| T90 | 358 |
| EP | 460 |
| API gravity | 55.6 |
| Cetane Index | 48 |
| Cetane number ($H^1$ nmr) | 20 |

After cooling, the residua were again distilled under vacuum (about 1–2 torr) to obtain a cut (13.9 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. Boiling Range (°F.) | |
| --- | --- |
| IBP | 308 |
| T10 | 375 |
| T50 | 475 |
| T90 | 578 |
| EP | 630 |
| API gravity | 45.7 |
| Cetane Index | 62 |
| Cetane Number (H$^1$ nmr) | 29 |
| wt. % Aromatics | 1.7 |

Example 2

This example was performed with the catalyst from the previous example by adjusting the reactor temperature to 350° F. at 600 psig. A pre-mixed isopentane/pentene-1 feed stream (molar ratio=9.7) then was introduced at a flow rate of 0.1 gm pentenes/gm MCM-58/hr. After passing pre-mixed feed through the reactor zone for 48.3 hrs, product was collected over the following 25.8 hrs. Product distributions were calculated from gc analyses of the gaseous and liquid products, and an additional simulated distillation ASTM 2887 of the liquid products. The total reactor effluent weight was 288.1 g (99.7% mass balance) and showed the following distribution:

| Component | weight % |
| --- | --- |
| C$_3$-minus | 0.00 |
| Isobutane | 0.33 |
| n-Butane | 0.01 |
| Isopentane | 87.89 |
| n-Pentane | 0.51 |
| Cyclopentane | 0.00 |
| C$_6$-paraffin | 0.80 |
| Methylcyclopentane | 0.04 |
| C$_4$-olefin | 0.00 |
| Butadiene | 0.00 |
| C$_5$-olefin | 0.49 |
| Cyclopentene | 0.00 |
| C$_6$-olefin | 0.12 |
| Methylcyclopentane and Benzene | 0.00 |
| C$_7$-plus | 9.82 |
| Total | 100.00 |

Conversion of total pentenes was 94.7%. Calculated yields isobutane and C$_6$-plus components per pentenes converted (wt/wt) were:

| Fraction | Yields |
| --- | --- |
| C$_5$ | 0.04 |
| C$_6$–300° F. | 0.28 |
| 300–400° F. | 0.38 |
| 400–650° F. | 0.54 |
| above 650° F. | 0.04 |
| Total | 1.28 |

About 25 g of squalene was added to a portion of the liquid product (31.3 g) to serve as a high boiling "chaser" during fractional microdistllation. After distilling the sample to a 300° F. endpoint at ambient atmospheric pressure, the residua were fractionated under vacuum (about 55 torr) to obtain a cut (8.9 g) with the intended kerojet boiling range from 300° F. to 400° F. The actual boiling range for this cut was estimated by simulated distillation analysis ASTM 2887. The boiling range and product properties for this sample were:

| Intended cut 300–400° F. Boiling Range (°F.) | |
| --- | --- |
| BP | 143 |
| T10 | 270 |
| T50 | 320 |
| T90 | 348 |
| EP | 440 |
| API gravity | 59.5 |
| Cetane Index | 55 |
| Cetane Number (H$^1$ nmr) | 31 |

After cooling, the residua were again distilled under vacuum (about 1–2 torr) to obtain a cut (13.4 g) with the intended diesel fuel boiling range from 400° F. to 650° F. The actual boiling range for this cut was estimated by simulated distillation analysis ASTM 2887. The boiling range and product properties for this sample were:

| Intended cut 400–650 400–650° F. Boiling Range (°F.) | |
| --- | --- |
| IBP | 309 |
| T10 | 380 |
| T50 | 490 |
| T90 | 600 |
| EP | 672 |
| API gravity | 46.5 |
| Cetane Index | 65 |
| Cetane Number (H$_1$ nmr) | 33 |
| wt % Aromatics | 0.8 |

Changes and modifications in the specifically described embodiments can be carried out without departing from the scope of the invention which is intended to be limited only by the scope of the appended claims.

What is claimed is:

1. A process for converting feedstock comprising at least one olefin and at least one isoparaffin to product comprising distillate which comprises contacting said feedstock at conversion conditions with a catalyst composition comprising a porous crystalline material having the structure of MCM-58.

2. The process of claim 1, wherein said distillate contains less than about 35 wt. % aromatics.

3. The process of claim 1, wherein said distillate contains less than about 10 wt. % aromatics.

4. The process of claim 1, wherein said distillate has a cetane index of at least about 35.

5. The process of claim 1, wherein said distillate has a cetane index of at least about 45.

6. The process of claim 1, wherein the product boiling at a cut point up to about 450° F. is recycled to the contacting step.

7. The process of claim 1, wherein the product boiling at a cut point up to about 390° F. is recycled to the contacting step.

8. The process of claim 1, wherein said product further comprises gasoline.

9. The process of claim 1, wherein said conversion conditions include a temperature in the range of from about 100°–500° F.; a pressure in the range of from about 0 to about 1500 psig; an olefin WHSV (on zeolite basis) in the range of from about 0.01 to 10; and an isoparaffin:olefin molar ratio in the feedstock in the range of from about 0.1–100.

10. The process of claim 1, wherein said conversion conditions include a temperature in the range of from about 200°–400° F.; a pressure in the range of from about 50 to about 100 psig; an olefin WHSV (on zeolite basis) in the range of from about 0.1 to 5; and an isoparaffin:olefin molar ratio in the feedstock in the range of from about 0.25 to about 50.

11. The process of claim 1, wherein said at least one olefin is selected from the group consisting of $C_3$–$C_{10}$ olefins.

12. The process of claim 11, wherein said at least one olefin is selected from the group consisting of $C_4$–$C_8$ olefins.

13. The process of claim 1, wherein said at least one isoparaffin is selected from the group consisting of $C_4$–$C_8$ isoparaffins.

14. The process of claim 13 wherein said at least one isoparaffin is selected from the group consisting of $C_4$–$C_5$ isoparaffins.

15. A process for converting a feedstock comprising at least one olefin and at least one isoparaffin to product comprising gasoline which comprises contacting said feedstock under conversion conditions with a catalyst composition comprising a porous crystalline material having the structure of MCM-58.

16. A process for converting a feedtsock comprising at least one olefin and at least one isoparaffin to product comprising both distillate and gasoline which comprises contacting said feedstock under conversion conditions with a catalyst comprising a porous crystalline material having the structure of MCM-58.

* * * * *